(12) United States Patent
Massaro et al.

(10) Patent No.: US 10,028,491 B2
(45) Date of Patent: Jul. 24, 2018

(54) INSECT EGG CONVEYOR

(71) Applicant: Verily Life Sciences LLC, Mountain View, CA (US)

(72) Inventors: Peter Massaro, Belmont, CA (US); Robert Sobecki, Mountain View, CA (US); Tiantian Zha, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 148 days.

(21) Appl. No.: 15/272,748

(22) Filed: Sep. 22, 2016

(65) Prior Publication Data

US 2018/0077911 A1 Mar. 22, 2018

(51) Int. Cl.
| | |
|---|---|
| *A01K 67/033* | (2006.01) |
| *B65G 15/30* | (2006.01) |
| *B65G 35/04* | (2006.01) |
| *B65G 47/76* | (2006.01) |
| *B65G 49/04* | (2006.01) |
| *G01G 11/00* | (2006.01) |
| *H04N 7/18* | (2006.01) |
| *B65G 39/00* | (2006.01) |

(52) U.S. Cl.
CPC ............ *A01K 67/033* (2013.01); *B65G 15/30* (2013.01); *B65G 35/04* (2013.01); *B65G 39/00* (2013.01); *B65G 47/763* (2013.01); *B65G 49/0418* (2013.01); *G01G 11/003* (2013.01); *H04N 7/18* (2013.01)

(58) Field of Classification Search
USPC .................................................. 119/6.6, 6.8
See application file for complete search history.

(56) References Cited

U.S. PATENT DOCUMENTS

| | | | |
|---|---|---|---|
| 3,847,113 A | 11/1974 | Andreev et al. | |
| 3,941,089 A | 3/1976 | Andreev et al. | |
| 4,411,220 A | 10/1983 | Voegele et al. | |
| 4,765,274 A * | 8/1988 | Pizzol | A01K 67/033 |
| | | | 119/6.6 |
| 5,484,504 A * | 1/1996 | Tedders, Jr. | A01C 1/042 |
| | | | 118/308 |
| 5,759,224 A | 6/1998 | Olivier | |
| 2008/0044260 A1 | 2/2008 | Miyatani et al. | |
| 2009/0242469 A1 | 10/2009 | Calabrese | |

FOREIGN PATENT DOCUMENTS

GB     2174907     11/1986

OTHER PUBLICATIONS

International Patent Application No. PCT/US2017/045770, "International Search Report", dated Nov. 6, 2017, 12 pgs.

* cited by examiner

*Primary Examiner* — Yvonne R Abbott-Lewis
(74) *Attorney, Agent, or Firm* — Kilpatrick Townsend & Stockton LLC

(57) ABSTRACT

Example insect egg conveyors are disclosed. One example insect egg conveyor device includes multiple rollers positioned along a path and a drive unit that includes a motor connected to a roller of the multiple rollers to drive the roller and rotate the roller. The device also includes a substrate positioned on the roller and a fluid source positioned along the path. The rollers are arranged to move the substrate along the path and toward the fluid source in response to the motor rotating the roller.

24 Claims, 4 Drawing Sheets

INSECT EGG CONVEYOR

FIELD

The present disclosure generally relates to insect oviposition and more specifically to an insect egg conveyor.

BACKGROUND

Mosquitos oviposition refers to the process by which a female mosquito lays or deposits mosquito eggs. Many female mosquitos oviposit by flying over a body of water and laying eggs on the surface of the body of water. In some instances, mass rearing of insects such as, for example, mosquitos, can include using various methods, techniques, and devices to manage the oviposition process or the production of insect eggs or larva.

SUMMARY

Various examples are described for an insect egg conveyor.

In one example, a system according to the present disclosure includes: a roller positioned along a conveyor path; a hydrophilic substrate positioned on the roller; a fluid source positioned on the conveyor path to apply a fluid to the hydrophilic substrate; and a drive unit comprising a motor coupled to the roller to drive the roller and rotate the roller and move the hydrophilic substrate along the conveyor path and past the fluid source.

In one example, a method according to the present disclosure includes: positioning a hydrophilic substrate on a roller of an insect egg conveyor, the roller to move the hydrophilic substrate along a conveyor path; positioning a fluid source on the conveyor path; rotating the roller to move the hydrophilic substrate along the conveyor path, toward the fluid source, and through the insect chamber, wherein rotating the roller comprises driving, by a drive unit comprising a motor coupled to the roller, the roller to cause the roller to rotate; and collecting eggs laid on the hydrophilic substrate by an insect in the insect chamber.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of an insect egg conveyor. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Example of an Insect Egg Conveyor

One illustrative example of an insect egg conveyor includes multiple rollers, a substrate (e.g., paper), a bath (e.g., a vessel or container) that includes an amount of a fluid, and a drive unit.

An insect egg conveyor, in this illustrative example, is used to provide a continuous, moving strip of paper on which female mosquitos can lay eggs. A motor of the drive unit slowly rotates a series of rollers, which slowly dispenses paper from a roll and moves the paper along the rollers. In this illustrative example, the insect egg conveyor is positioned near a cage with a mosquito population. As the paper moves along the rollers, it travels into a water bath where the paper is wetted to create a suitable environment on which a mosquito may lay eggs. The paper then continues travel into the cage, where mosquitos are able to land on the paper and lay eggs. The paper, with the eggs, then continues to travel out of the cage, where the eggs can be harvested and moved into containers where the eggs can be incubated and hatch into larvae.

This illustrative example is given to introduce the reader to the general subject matter discussed herein and the disclosure is not limited to this example. The following sections describe various additional non-limiting examples and examples of systems and methods for insect egg conveyors.

Figure 1:
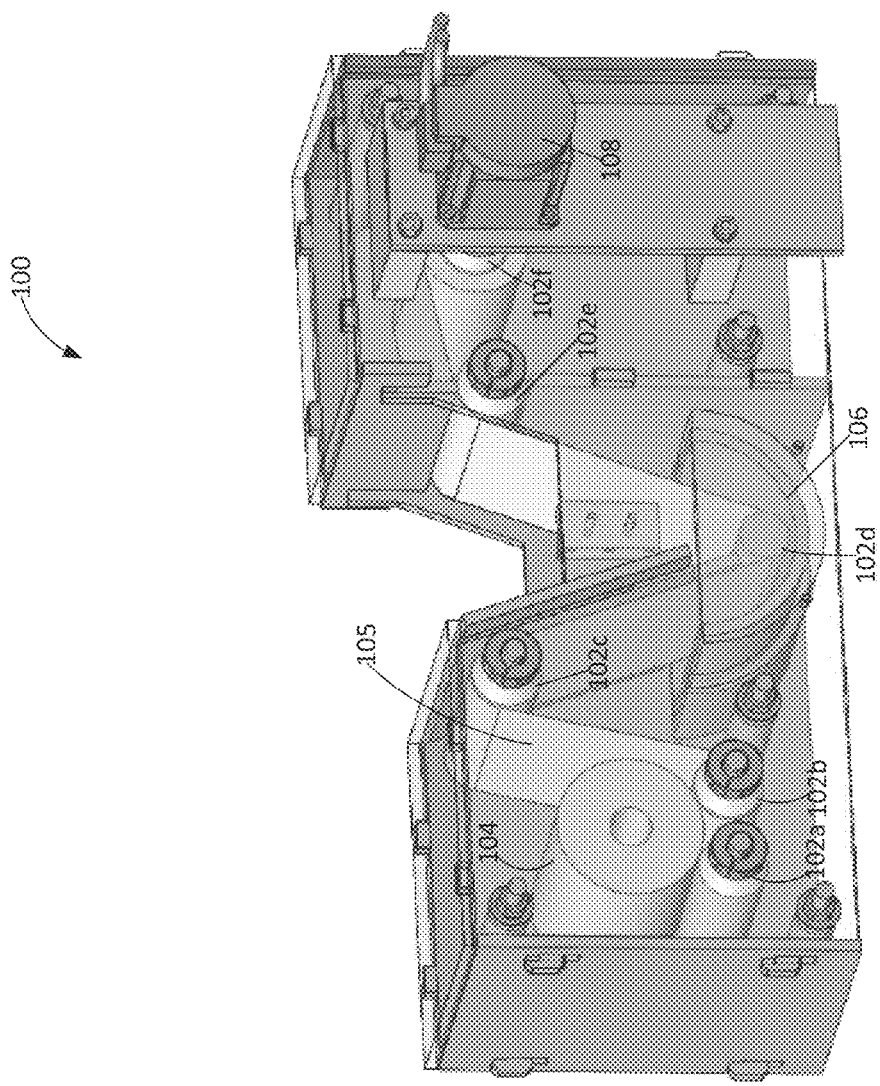
FIG. 1 shows an example of an insect egg conveyor.

FIG. 1 shows an example of insect egg conveyor 100. The insect egg conveyor 100 includes multiple rollers 102*a-f*, a substrate 104, a fluid source 106, and a drive unit 108. Each of the rollers 102*a-f* is a cylindrical roller that can be made of any suitable material for moving a substrate (e.g., the substrate 104) along a path. For example, each roller 102*a-f* can be a plastic roller, or a roller of any other suitable material for moving a dispensed substrate 105 (e.g., a dispensed portion of the substrate 104) along a path from one roller to another roller. In this example, each roller 102*a-f* is depicted as a cylinder having a circular cross-section, as may be seen in FIG. 1; however, suitable rollers may have any suitable cross section for a given application.

The substrate 104 can be a hydrophilic surface, a fabric, or any other suitable substrate or material including, for example, paper, filter paper, felt, or nylon cloth. A hydrophilic substrate or surface can include any material that can mix with, dissolve in, or be wetted or dampened by a fluid such as, for example, water. In some examples, a portion of the substrate 104 can be positioned on, or wound around, one or more of the rollers 102*a-f*. In the example shown in FIG. 1, a first portion of the substrate 104 is positioned on the rollers 102*a-b* and a second portion of the substrate 104 is wound around the roller 102*f*. In some examples, the substrate 104 can be positioned on, wound around, or otherwise disposed on one or more of the rollers 102a-f in any manner, including without limitation, manually (e.g., by manually positioning or disposing the substrate 104 on one of rollers 102a-f) or through automated disposal (e.g., by an apparatus, device, machine, or the like that can dispose or position the substrate 104 on one of rollers 102a-f).

The fluid source 106 can include a bath, housing, container, or chamber that includes an amount of a fluid such as, for example, water. In another example, the fluid source 106 can include a device that can provide or dispense an amount of fluid (e.g., a pump, nozzle, or spray device that can provide or dispense fluid). In some examples, the fluid source 106 can be positioned between the rollers 102a-f, which can allow the dispensed substrate 105 of the substrate 104 to contact fluid in the fluid source 106 or fluid provided by the fluid source 106. For example, in the example depicted in FIG. 1, the fluid source 106 is positioned between the roller 102c and the roller 102e and roller 102d is positioned within the fluid source 106 to allow the dispensed substrate 105 to pass through the fluid in the fluid source 106. In some examples, the dispensed substrate 105 travels past the fluid source 106 and is sprayed or dripped with fluid from the fluid source 106.

In some examples, positioning a portion of the substrate 104 on one of the rollers 102a-f or winding a portion of the substrate 104 around one of the rollers 102a-f can allow the substrate 104 to be drawn along a path between the rollers 102a-f as the rollers 102a-f rotate. For example, at least one of the rollers 102a-f can be coupled to the drive unit 108, which can include a motor, transmission, or other device for applying a force to the rollers 102a-f to drive them and cause them to rotate. Rotating the rollers 102a-f can cause the substrate 104 to rotate in a similar manner as the rollers 102a-f, which can cause the substrate 104 to unroll or unwind and allow the dispensed substrate 105 to travel along the path between the rollers 102a-f. As an example, in the example depicted in FIG. 1, the drive unit 108 is connected to the roller 102f and can apply a rotational force to the roller 102f to cause the roller 102f to rotate clockwise or counterclockwise, depending on the arrangement of the substrate 104 and the rollers 102a-f. Rotating the roller 102f clockwise or counterclockwise causes the portion of the substrate 104 wound around the roller 102f to rotate in a corresponding manner. For example, rotating the roller 102f clockwise causes the portion of the substrate 104 wound around the roller 102e to rotate in a clockwise direction, which causes the dispensed substrate 105 to travel along a path from the rollers 102a-b toward the roller 102f.

The dispensed substrate 105 travels along the path between the rollers 102a-f and passes through the fluid source 106, which causes the dispensed substrate 105 to contact fluid in the fluid source 106 or dispensed by the fluid source 106 and become damp or wet. For example, the roller 102f can rotate in a clockwise direction as described above, which can cause the dispensed substrate 105 to travel from the rollers 102a-b toward the roller 102f. In the example depicted in FIG. 1, the fluid source 106 is positioned in the path of the dispensed substrate 105, which can allow a portion of the dispensed substrate 105 to contact the fluid in the fluid source 106 or dispensed by the fluid source as the dispensed substrate 105 travels along the path from the rollers 102a-b toward the roller 102f.

In some examples, the insect egg conveyor 100 can be placed proximate to a housing or cage that includes one or more mosquitos. For example, the insect egg conveyor 100 or a component of the insect egg conveyor 100 can be placed within the housing or cage. In such examples, dampening or wetting the dispensed substrate 105 prior to the dispensed substrate 105 entering the housing can allow a mosquito in the housing to oviposit (e.g., lay an egg) on, or proximate to, the wet dispensed substrate 105. In this illustrative embodiment, the drive unit 108 can continuously drive the rollers 102a-f to allow one or more portions of the dispensed substrate 105 to contact the fluid in the fluid source 106 or fluid dispensed by the fluid source 106, which can provide multiple wet or damp sites on the dispensed substrate 105 near which one or more mosquitos in the housing can oviposit. In some such examples, the substrate 104 may be disposed of after use over any suitable period of time. In other examples, the substrate 104 may be reusable (e.g., the substrate 104 may be re-wound around one or more rollers 102a-f after a mosquito oviposits on the dispensed substrate 105 and the drive unit 108 can drive one of the rollers 102a-f to cause the dispensed substrate 105 to again travel along a path toward the housing). In some examples, the housing or cage that contains one or more mosquitos can be positioned proximate to the fluid source 106, which can expose the mosquitos to the fluid in the fluid source 106 or dispensed by the fluid source 106 and attract the mosquitos to the wet or damp substrate 105 on which the mosquitos can oviposit. In some examples, fluid in the fluid source 106 can be used (e.g., dispensed by the fluid source 106 or remain in the fluid source 106) over any desired period of time. In other examples, fluid in the fluid source 106 may be disposable after use over any suitable period of time.

While in some examples, the insect egg conveyor 100 can be placed proximate to a housing or cage that includes one or more mosquitos, in other examples, the insect egg conveyor may not be placed proximate to the housing or cage that includes a mosquito. Rather, in some examples, the mosquito housing or cage may not be positioned near the insect egg conveyor 100 or mosquitos within the housing or cage may be prevented from accessing the insect egg conveyor 100. In such examples, mosquito eggs deposited on the dispensed substrate 105 may be collected and the substrate 104 may be wound around one or more rollers 102a-f while the mosquitos do not have access to the mosquito egg conveyor 100.

In some examples, drive unit 108 can control a rate or speed at which one or more of the rollers 102a-f rotates, which can affect a speed or velocity at which the dispensed substrate 105 travels along a path between the rollers 102a-f. For example, the drive unit 108 can be communicatively coupled to a remote device (e.g., the computing device 300 of FIG. 1 described in more detail below) and the remote device can transmit a signal to the drive unit 108. The signal can indicate a rotational speed of the drive unit 108, which can affect a speed or rate at which one or more of the rollers 102a-f will rotate. As an example, the rotational speed of the drive unit 108 can affect the speed or rate that the roller 102f rotates, and the speed or rate at which the roller 102f rotates can affect the speed or velocity with which the dispensed substrate 105 travels along the path between the rollers 102a-f. As an illustrative example, the signal transmitted from the remote device can cause the drive unit 108 to rotate at a rotational speed such that the roller 102f is rotated to cause the dispensed substrate 105 to travel from the roller 102a toward the roller 102f at a rate of one-half inch per hour. While in some examples, the dispensed substrate 105 can travel from the roller 102a toward the roller 102f at a rate of one-half inch per hour, the present disclosure is not limited to such configurations. Rather, the dispensed substrate 105 can travel between the rollers 102a-f at any speed or rate based on the application or use of the insect egg conveyor 100. For example, the rotational speed of the drive unit 108 or the speed of the dispensed substrate 105 may vary based on a willingness of a particular insect (e.g., a species of mosquitos) in the housing to oviposit on the dispensed substrate 105 moving at a particular speed.

In this manner, the remote device (not shown) can transmit signals to the drive unit 108 to control the rate at which the dispensed substrate 105 travels between the rollers 102a-f and through the housing that includes mosquitos, such that a damp or wet portion of the dispensed substrate 105 can be accessible to the mosquitos for any desired period of time to allow the mosquitos to oviposit during the period of time. While in some examples, the insect egg conveyor 100 can be used to provide a damp or wet substrate on which a mosquito can oviposit, the present disclosure is not limited to such applications. Rather, the insect egg conveyor 100 can be used to provide a site on which any insect can oviposit.

Although a certain number of rollers 102a-f and fluid source 106 are depicted in FIG. 1, in some examples, the insect egg conveyor 100 may include any number of rollers of the same or different types or any number of baths. Moreover, although in the example depicted in FIG. 1, a size of one or more rollers 102a-f is depicted as smaller, or larger, than a size of other rollers 102a-f, in some examples, each roller 102a-f can be of any size depending on the application or use of the insect egg conveyor 100.

Figure 2:
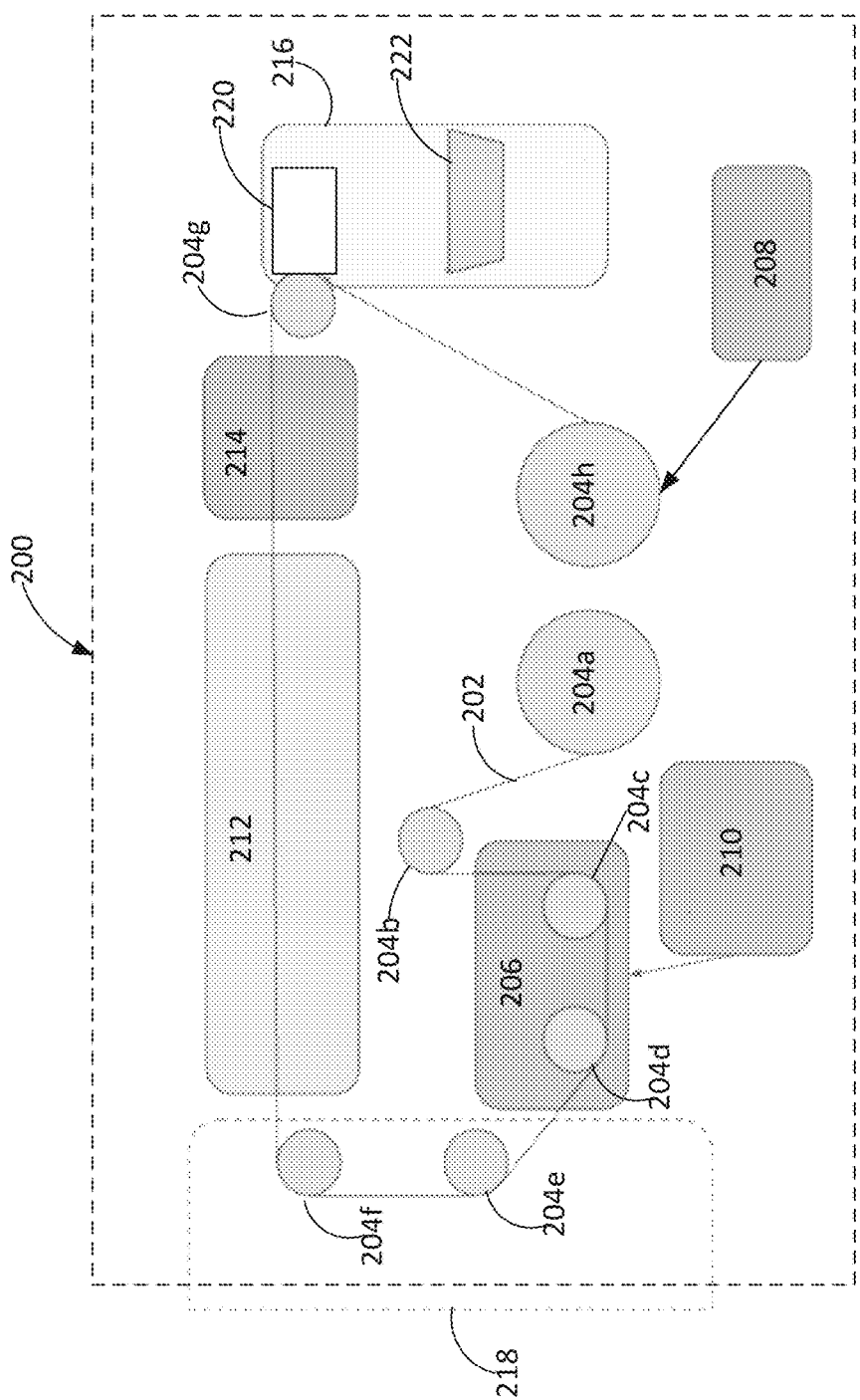
FIG. 2 shows another example of an insect egg conveyor.

Further, in some examples, insect egg conveyors may include one or more additional components. For example, FIG. 2 shows another example of an insect egg conveyor 200. The insect egg conveyor 200 shown in FIG. 2 includes a substrate 202, rollers 204a-h, a fluid source or bath 206, and a drive unit 208. In this example, the insect egg conveyor 200 also includes a reservoir 210, an environmentally-controlled chamber 212, a sensor 214, and a collection unit 216. In the example depicted in FIG. 2, the insect egg conveyor 200 or one or more components of the insect egg conveyor 200 can be arranged to pass the substrate 202 through a portion of the housing 218.

Each of the rollers 204a-h is a cylindrical roller for moving the substrate 202 along a path between the rollers 204a-h. For example, the substrate 202 can be positioned on one or more of the rollers 204a-h and the drive unit 208 can cause the rollers 204a-h to rotate and move the substrate 202 from roller 204a toward the roller 204h. The substrate 202 can be any hydrophilic substrate or any suitable substrate such as, for example, paper, felt, or nylon cloth. While in the example depicted in FIG. 2, a size of one or more rollers 204a-h is depicted as smaller, or larger, than a size of other rollers 204a-h, in some examples, each roller 204a-h can be of any size for various examples according to this disclosure.

In this example, the fluid source or bath 206 includes an amount of a fluid (e.g., water) and the bath 206 is positioned between rollers 204a-h. In the example depicted in FIG. 2, the bath 206 is positioned between the roller 204b and the roller 204e. The bath 206 is connected to the reservoir 210, which can include a fluid (e.g., water). In some examples, the fluid in the reservoir 210 can be dispensed into the bath 206 for replenishing an amount of the fluid in the bath 206. For example, the reservoir 210 may include a pump for dispensing the fluid in the reservoir 210 into the bath 206. In some examples, the insect egg conveyor 200 can include one or more components for causing fluid in the reservoir 210 to be automatically dispensed into the bath 206. As an example, the bath 206 can include one or more sensors for detecting an amount of the fluid in the bath 206 and the sensors may be communicatively coupled to a remote device (e.g., the computing device 300 of FIG. 3) for transmitting sensor signals indicating the amount of the fluid in the bath 206 to the remote device. The remote device can then transmit one or more signals to the reservoir 210 or a component of the reservoir 210 (e.g., a switch in the reservoir 210) based on the amount of the fluid in the bath 206 and the signals can cause the reservoir 210 to dispense fluid in the reservoir 210 into the bath 206. For example, the sensor signals transmitted to the remote device can indicate that the amount of water in the bath 206 is below a threshold and the remote device can transmit a signal to the reservoir 210 to cause the reservoir 210 to dispense water in the reservoir 210 into the bath 206 to replenish the bath 206.

The drive unit 208 applies a force to one or more of the rollers 204a-h to drive the roller 204a-h and cause it to rotate. In the example depicted in FIG. 2, the drive unit 208 applies a force to the roller 204h to rotate the roller 204h. Further, in this example, a portion of the substrate 202 is positioned on one or more of the rollers 204a-h to allow the rollers 204a-h to draw the substrate 202 along a path between the rollers 204a-h as the rollers 204a-h rotate. As an example, a portion of the substrate 202 is positioned on the rollers 204a-h and rotating the roller 204h causes the substrate 202 to unwind and travel along a path between the rollers 204a-h (e.g., along a path from the roller 204a toward the roller 204h).

In some examples, the bath 206 can be positioned in the path of the substrate 202 to allow a portion of the substrate 202 to contact fluid within the bath 206 as the substrate 202 travels along the path from the roller 204a toward the roller 204h. In the example depicted in FIG. 2, the bath 206 is positioned between the rollers 204b and 204e and a portion of the substrate 202 can contact the fluid in the bath 206 as the substrate 202 travels from the roller 204b toward the roller 204e. In this manner, a portion of the substrate 202 can become damp or wet as the portion moves from the roller 204b toward the roller 204e.

In this example, one or more of the components of the insect egg conveyor 200 are positioned proximate to the housing 218. For example, each of the rollers 204e-f is positioned within the housing 218 and the bath 206 is positioned in the path of the substrate 202 prior to the housing 218. In some examples, positioning the housing 218 in the path of the substrate 202 subsequent to the bath 206 can allow the insect egg conveyor 200 to provide a damp or wet portion of the substrate 202 on or near which a mosquito within the housing 218 can oviposit as the portion of the substrate 202 travels through the housing 218 (e.g., as the portion of the substrate 202 travels between the rollers 204d-f). In some examples, the drive unit 208 can continuously apply a force to drive one or more of the rollers 204a-h to cause multiple (e.g., sequential) portions of the substrate 202 to contact fluid in the bath 206 as the substrate 202 travels from the roller 204a toward the roller 204h, which can provide multiple wet or damp sites on the substrate 202 near which the one or more mosquitos in the housing 218 can oviposit as the substrate 202 travels through the housing 218.

The insect egg conveyor 200 also includes the environmentally-controlled chamber 212, which can be a housing or chamber for receiving the substrate 202 after the substrate 202 travels through the housing 218 and the environmentally-controlled chamber 212 can include one or more components for adjusting a parameter of the environment or atmosphere within the environmentally-controlled chamber 212. For example, the environmentally-controlled chamber 212 can include one or more devices for adjusting a temperature or humidity within the environmentally-controlled chamber 212. As an example, the environmentally-controlled chamber 212 can include a humidifier, a de-humidifier, or any other suitable device for increasing or decreasing a humidity level within the environmentally-controlled chamber 212. In such examples, the humidifier, de-humidifier, or other device may adjust a humidity level within the environmentally-controlled chamber 212 as a portion of the substrate 202 that includes one or more mosquito eggs (e.g., a damp portion of the substrate 202 near which a mosquito has laid an egg) travels through the environmentally-controlled chamber 212. As another example, the environmentally-controlled chamber 212 can include a drying device, a heating device, or any suitable device for providing an amount of heat within the environmentally-controlled chamber 212 to dry one or more mosquito eggs on a damp or wet portion of the substrate 202 as the portion of the substrate 202 passes through the environmentally-controlled chamber 212. In some examples, the devices within the environmentally-controlled chamber 212 can be used to adjust the parameter of the environment within the environmentally-controlled chamber 212 as the substrate 202 travels through the environmentally-controlled chamber 212. In this manner, the environmentally-controlled chamber 212 can include one or more components for adjusting environmental conditions within the environmentally-controlled chamber 212 as mosquito eggs on the substrate 202 travel through the environmentally-controlled chamber 212, which can enhance one or more processes for mass rearing the mosquitos (e.g., by providing suitable environmental conditions for rearing the mosquito eggs or larva on a portion of the substrate 202 passing through the environmentally-controlled chamber 212).

The sensor 214 can include one or more devices that can detect or provide data about an amount of mosquito eggs on a portion of the substrate 202. For example, the sensor 214 can include one or more cameras configured to capture images the substrate 202 as it passes by the camera. In some examples, the sensor 214 can capture an image of a portion of the substrate 202 that includes one or more mosquito eggs. Such a sensor 214 can be communicatively coupled to a remote device (e.g., the example computing device 300 of FIG. 3) and the sensor 214 can transmit image data to the remote device, which can then determine an amount of mosquito eggs on the substrate 202 based on the image data. As another example, the sensor 214 can include a scale or other suitable device for detecting a weight of a portion of the substrate 202. In such examples, the sensor 214 can detect a weight of a portion of the substrate 202 that includes one or more mosquito eggs and the sensor 214 can be communicatively coupled to the remote device to transmit data that indicates the weight to the remote device for determining the amount of mosquito eggs on the portion of the substrate 202. For example, the remote device may include data about a weight of a portion of the substrate 202 prior to the portion of the substrate 202 traveling through the housing 218 (e.g., if a user programs the remote device to include the data). The sensor 214 can detect a weight of the portion of the substrate 202 after the portion travels through the housing 218 and transmit data to the remote device indicating a weight of the portion of the substrate 202 after the portion travels through the housing 218. The remote device can compare the weight of the portion of the substrate 202 before and after traveling through the housing 218 to determine a weight of one or more mosquito eggs on the portion of the substrate 202, which can be used to determine an amount of mosquito eggs on the portion of the substrate 202.

In some examples, the sensor 214 can transmit a time stamp or time indicator associated with sensor data to the remote device, which can determine an amount of mosquito eggs laid on a portion of the substrate 202 over a time period. For example, the sensor 214 can include a camera that captures an image of a portion of the substrate 202 and transmits image data to the remote device as described above. The sensor 214 can also transmit a time stamp associated with the image data (e.g., a time stamp indicating a time that the image is captured). The remote device can receive multiple images and time stamps associated with each image over a period of time (e.g., five minutes or any other suitable time period) and analyze the images and time stamps to determine an amount of mosquito eggs laid on the substrate 202 over the period of time. As another example, the sensor 214 includes a scale or other pressure sensor that detects a pressure exerted by a portion of the substrate 202 and transmits data about the detected pressure, e.g., a corresponding weight, to the remote device as described above. The sensor 214 can also transmit a time stamp associated with the detected weight of each portion of the substrate 202 (e.g., a time stamp indicating a time that the weight of the portion of the substrate 202 is detected). The remote device can receive data about the detected weight of multiple portions of the substrate 202 and time stamps associated with the detected weight of each portion of the substrate 202 over a period of time and analyze the detected weights and time stamps to determine an amount of mosquito eggs laid on the substrate 202 over the period of time.

While in some examples, the sensor 214 can transmit a time stamp associated with sensor data, which can be used to determine an amount of mosquito eggs laid on a portion of the substrate 202 over a period of time as described above, the present disclosure is not limited to such configurations. Rather, in some examples, the substrate 202 can be marked with a time-stamp (e.g., marked manually or by an apparatus, device, or machine) to determine an amount of mosquito eggs laid on a portion of the substrate 202 over a period of time. For example, a first portion of the substrate 202 can be marked with a first time stamp (e.g., a time or date) and a second portion of the substrate 202 can be marked with a second time stamp. The amount of mosquito eggs on the first and second portions can be determined as described above and the amount of mosquito eggs laid on the substrate 202 over the time period between the first time stamp and the second time stamp can be determined by comparing the amount of mosquito eggs on the first and second portions, the first time stamp, and the second time stamp (e.g., using the remote device).

The insect egg conveyor 200 also includes the collection unit 216, which includes one or more devices that can remove or collect a mosquito egg from the substrate 202. For example, the collection unit 216 can include a removal device 220 for removing the mosquito egg from the substrate 202 and a container 222 (e.g., a bin) for collecting the mosquito egg as the removal device 220 removes the mosquito egg from the substrate 202.

As an example, the removal device 220 is a brush or a scraper positioned proximate to the path of the substrate 202 for sweeping one or more mosquito eggs from a surface of the substrate 202. For example, the removal device 220 can be positioned proximate to the roller 204g for sweeping one or more mosquito eggs from the surface of the substrate 202 as the substrate 202 travels from the roller 204g toward the roller 204h. As another example, the removal device 220 can include an air blowing device that displaces air near the substrate 202 or blows air across the surface of the substrate 202 for removing one or more mosquito eggs from the surface of the substrate 202 (e.g., by blowing the air near the substrate 202 to displace the mosquito eggs from the surface of the substrate 202). In some examples, the air blowing device may blow deionized air toward the substrate 202 for removing one or more mosquito eggs from the surface of the substrate 202. In the example depicted in FIG. 2, the container 222 can be positioned proximate to the path of the substrate 202 and proximate to the removal device 220 for collecting at least a subset of the mosquito eggs removed from the surface of the substrate 202 by the removal device 220. In some examples, the container 222 can also include a scale for detecting a weight of the subset of the mosquito eggs for determining an amount of mosquito eggs in the subset. For example, the container 222 can detect a weight of the subset of the mosquito eggs and data indicating the weight can be transmitted to a remote device that can determine an amount of the mosquito eggs based on the weight.

Although a certain number of components of the insect egg conveyor 200 are depicted in FIG. 2, in some examples, the insect egg conveyor 200 may include any number or types of rollers, baths, drive units, reservoirs, environmentally-controlled chambers, sensors, collection units, etc. Moreover, in some examples, one or more components depicted in FIG. 2 may not be included in the insect egg conveyor 200. Further, in some examples, one or more housings that include at least one mosquito may be positioned proximate to the insect egg conveyor 200. Also, while in some examples, the insect egg conveyor 200 can be used to provide a damp or wet substrate on which a mosquito can oviposit, the present disclosure is not limited to such applications. Rather, the insect egg conveyor 200 can be suitable for use with any insect.

Figure 3:
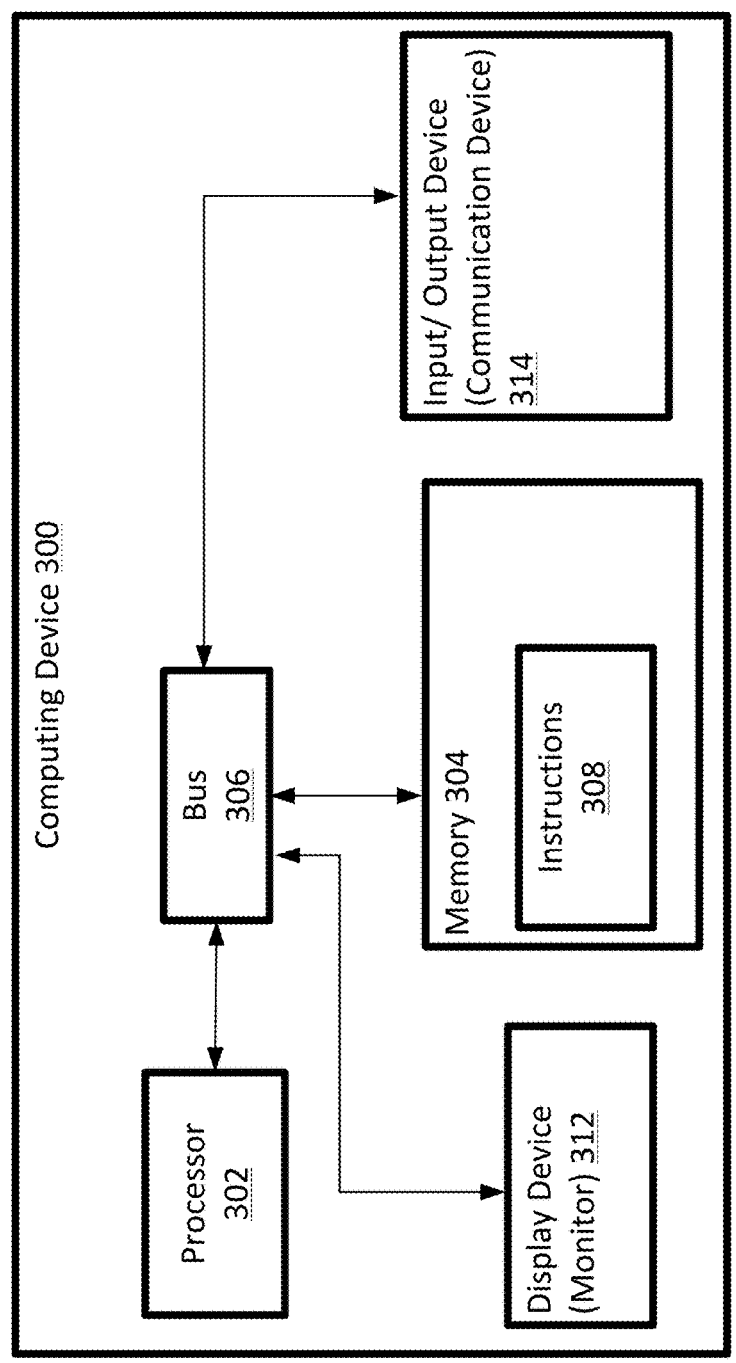
FIG. 3 shows a block diagram of an example of a computing device suitable for use with insect egg conveyors according to this disclosure.

FIG. 3 shows a block diagram of an example of a computing device 300 that can be communicatively coupled to an insect egg conveyor. The computing device 300 will be described with respect to the example insect egg conveyor 200 shown in FIG. 2; however, the computing device 300 is not limited to such an insect egg conveyor 200. Rather, the computing device 300 may be communicatively coupled to any suitable insect egg conveyor according to this disclosure.

The computing device 300 can be communicatively coupled to one or more components of the insect egg conveyor 200 for transmitting and receiving data and can include a processor 302, a memory 304, and a bus 306. The memory 304 can also include instructions 308 executable by the processor 302 for operating the computing device 300. The computing device 300 can also include a display device 312, and a communication device 314.

The processor 302 can be communicatively coupled to the memory 304 via the bus 306. The memory 304 can include any type of memory device that retains stored information when powered off. The computing device 300 uses the processor 302 and the memory 304 to execute software for obtaining information from the insect egg conveyor 200 and store such information in the memory 304. The computing device 300 can also use the processor 302 and the memory 304 to execute software for transmitting information to the insect egg conveyor 200. The display device 312 can provide a user interface and can provide information that has been obtained from the insect egg conveyor 200.

The communication device 314 may be wireless and can include wireless interfaces such as IEEE 802.11, BlueTooth, a wireless local area network ("WLAN") transceiver, or radio interfaces for accessing cellular telephone networks (e.g., transceiver/antenna for accessing a CDMA, GSM, UMTS, or other mobile communications network). In another example, the communication device 314 can be wired and can include interfaces such as Ethernet, USB, or IEEE 1394. In some examples, the computing device 300 may communicate (e.g., transmit and receive data) via the communication device 314.

In some examples, the instructions 308 can configure the processor 302 to transmit a signal to a drive unit 208 of the insect egg conveyor 200 to control a rotational speed of the drive unit 208. For example, the instructions 308 may cause the processor 302 to access stored waveforms or commands to send to the drive unit 208 to cause the drive unit 208 to rotate at a particular rotational speed. As an example, the instructions 308 can cause the processor 302 to access a lookup table that includes data indicating one or more signals associated with one or more rotational speeds and determine a signal to transmit to the drive unit 208 to cause the drive unit 208 to rotate at a particular rotational speed. Thus, in some examples, the computing device 300 can transmit one or more signals to control a rotational speed of the drive unit 208, which, as described above, affects the speed or rate at which rollers 204a-h rotate and affects the speed or velocity with which the substrate 202 travels along a path between the rollers 204a-h. For example, the computing device 300 may transmit a signal to the drive unit 208 to cause the substrate 202 to move at a constant rate, e.g., 1-2 meters per minute. In some examples, though, the computing device 300 may transmit a signal to the drive unit 208 to cause the substrate 202 to move at a variable rate, e.g., based on a voltage or current of the drive signal or a pulse-width modulated signal.

In some examples, the instructions 308 can configure the processor 302 to receive sensor data from one or more components of the insect egg conveyor 200. For example, the processor 302 can receive sensor data from a sensor included in a bath 206 of the insect egg conveyor 200. The sensor data can indicate an amount of fluid (e.g., water) in the bath 206 and the processor 302 can execute processor executable instructions 308 to compare the amount of fluid in the bath 206 to a threshold amount of fluid (e.g., a threshold amount of fluid stored in the memory 304). In this illustrative example, the processor 302 can then transmit one or more signals to a reservoir 210 of the insect egg conveyor 200 based on the comparison. As an example, the processor 302 can transmit a signal to the reservoir 210 in response to determining that the amount of fluid in the bath 206 is below the threshold amount of fluid and the signal can cause the reservoir 210 to dispense a fluid (e.g., water) in the reservoir 210 into the bath 206. As another example, the processor 302 may not transmit a signal to the reservoir 210 in response to determining that the amount of fluid in the bath 206 is above the threshold amount of fluid and the reservoir 210 may not dispense fluid in the reservoir 210 into the bath 206.

As another example, the instructions 308 can configure the processor 302 to receive sensor data from a sensor 214 of the insect egg conveyor 200 and determine an amount of mosquito eggs on the substrate 202 based on the sensor data. For example, the sensor 214 can be a camera that captures an image of a portion of the substrate 202 that includes one or more mosquito eggs as the portion of the substrate 202 passes by the camera and transmits image data to the processor 302. The instructions 308 can configure the processor 302 to receive the image data and analyze the image data to determine an amount of mosquito eggs on the portion of the substrate 202. In another example, the instructions 308 can configure the processor 302 to receive the image data and output the image (e.g., via the display device 312) for determining the amount of mosquito eggs on the portion of the substrate 202. In still another example, the sensor 214 can be a scale that detects a weight of a portion of the substrate 202 that includes mosquito eggs and transmits weight data to the computing device 300. The instructions 308 can configure the processor 302 to access data in the memory 304 indicating a weight of the portion of the substrate 202 prior to the portion of the substrate 202 traveling through a housing 218 that includes one or more mosquitos. The instructions 308 can then configure the processor 302 to compare the weight of the portion of the substrate 202 that includes the mosquito eggs to the weight of the portion prior to the portion traveling through the housing 218 and the processor 302 can determine an amount of mosquito eggs on the portion of the substrate 202 based on the comparison.

In some examples, the instructions 308 can also configure the processor 302 to store information or data received from the insect egg conveyor 200 in the memory 304. For example, the computing device 300 receives sensor data from the sensor 214 and stores the sensor data in the memory 304. The computing device 300 may store the sensor data along with a time stamp or time indicator associated with the sensor data. As an example, the computing device 300 can receive image data corresponding to an image of a portion of the substrate 202 that includes mosquito eggs and a time stamp associated with the image, and store the image data, along with the time stamp in the memory 304. As another example, the computing device 300 can receive data indicating a detected weight of a portion of the substrate 202 that includes mosquito eggs and a time stamp associated with the detected weight, and store the detected weight, along with the time stamp in the memory 304. In some examples, the instructions 308 can cause the processor 302 to generate a time stamp associated with sensor data received by the computing device 300 when the computing device 300 receives the sensor data, but, in other examples, the computing device 300 receives the time stamp associated with the sensor data from the sensor 214.

In some examples, the processor 302 can execute instructions 308 to determine an amount of eggs laid on the substrate 202 over a period of time based on data received from the insect egg conveyor 200. For example, the computing device 300 can receive, from the sensor 214, multiple images of portions of the substrate 202 that each include mosquito eggs over a period of time (e.g., ten minutes) and a time stamp or a series of time stamps associated with the images (e.g., a time stamp indicating a length of the period of time or one or more time stamps corresponding to an interval of time within the period of time). The computing device 300 can store the images and the associated time stamps in the memory 304. The processor 302 can execute instructions 308 for analyzing one or more of the images and time stamps associated with the images to determine an amount of mosquito eggs laid on the substrate 202 over the period of time. As an example, the processor 302 can analyze a first image to determine a first amount of mosquito eggs laid on a first portion of the substrate 202 captured in the first image. The processor 302 can also analyze a second image to determine a second amount of mosquito eggs laid on a second portion of the substrate 202 captured in the second image. The processor 302 can compare a first time stamp associated with the first image and a second time stamp associated with the second image to determine a period of time between the first image and the second image. The processor 302 can then compare the first amount of mosquito eggs, the second amount of mosquito eggs, and the period of time between the first image and the second image to determine an amount of mosquito eggs laid on the substrate 202 over the period of time between the first image and the second image.

As another example, the computing device 300 can receive, from the sensor 214, data about weights of portions of the substrate 202 that include mosquito eggs over a period of time (e.g., five minutes) and a time stamp or a series of time stamps associated with the detected weights. The computing device 300 can store the data and the associated time stamps in the memory 304. The processor 302 can execute instructions 308 for comparing the time stamp associated with one or more detected weights to determine an amount of mosquito eggs laid on the substrate 202 over the period of time. As an example, the processor 302 can receive data about a detected weight of a first portion of the substrate 202 and determine a first amount of mosquito eggs on the first portion based on the weight as described above. The processor 302 can also receive data about a detected weight of a second portion of the substrate 202 and determine a second amount of mosquito eggs on the second portion based on the weight. The processor 302 can compare the first amount of mosquito eggs, the second amount of mosquito eggs, and a time stamp indicating an interval or period of time between detection of the weight of the first portion and detection of the weight of the second portion and determine an amount eggs laid on the substrate 202 over the period of time based on the comparison.

In some examples, the instructions 308 can configure the processor 302 to output information or data received from the insect egg conveyor 200 (e.g., from one or more sensors of the insect egg conveyor 200) via the display device 312.

Figure 4:
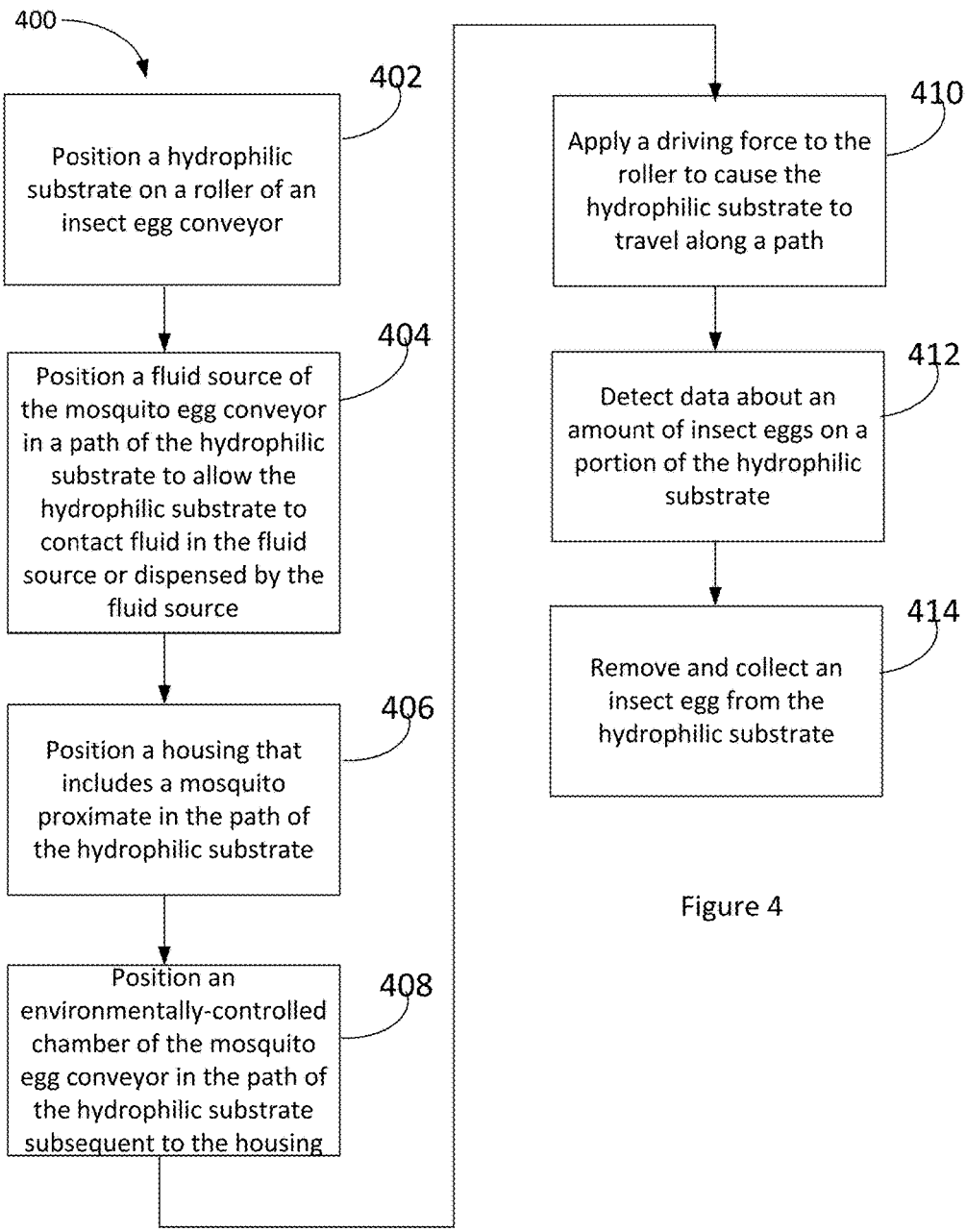
FIG. 4 shows an example of a method of using an insect egg conveyor.

FIG. 4 shows an example of a method 400 of using an insect egg conveyor. In some examples, one or more steps shown in FIG. 4 may be omitted or performed in a different order. Similarly, in some examples, additional steps not shown in FIG. 4 may also be performed. The method 400 of FIG. 4 will be described with respect to the example insect egg conveyor 200 shown in FIG. 2; however, the method 400 is not limited to such an insect egg conveyor 200. Rather, the method 400 may be performed with any suitable insect egg conveyor according to this disclosure.

At block 402, a substrate 202 is positioned on a roller of a plurality of rollers 204a-h of an insect egg conveyor 200. For example, a portion of the substrate 202 can be wound around or positioned on one or more of the rollers 204a-h. Examples of the substrate 202 include, but are not limited to, paper, felt, nylon cloth or any other suitable material.

Each of the rollers 204a-h is a cylindrical roll that can be made of any suitable material for rolling the substrate 202 along a path. For example, each roller 204a-h can be a plastic roller, or a roller of any other suitable material, for moving the substrate 202 along a path from one roller to another roller.

At block 404, a bath 206 of the insect egg conveyor 200 is positioned in the path of the substrate 202 to allow the substrate 202 to contact fluid in the bath 206. The bath 206 is a housing, container, or chamber that includes an amount of a fluid such as, for example, water. In some examples, the bath 206 can be positioned in the path of the substrate 202 and between rollers 204a-h to allow a portion of the substrate 202 to contact fluid within the bath 206 as the substrate 202 travels along the path from the roller 204a toward the roller 204h. In this manner, a portion of the substrate 202 can become damp or wet as the substrate 202 moves from the roller 204a toward the roller 204h.

At block 406, a housing 218 that includes a mosquito is positioned proximate to the insect egg conveyor 200. For example, the housing 218 can be positioned in the path of the substrate 202 between the rollers 204a-h and subsequent to the bath 206. In some examples, positioning the housing 218 in the path of the substrate 202 subsequent to the bath 206 can allow the mosquito within the housing 218 to oviposit on a wet or damp portion of the substrate 202 as the substrate 202 travels through the housing 218 (e.g., as the substrate 202 travels between the rollers 204d-f).

At block 408, an environmentally-controlled chamber 212 is positioned in the path of the substrate 202 subsequent to the housing 218. For example, the environmentally-controlled chamber 212 is a housing or chamber for receiving the substrate 202 after the substrate 202 travels through the housing 218. The environmentally-controlled chamber 212 includes one or more components for adjusting a parameter of the environment or atmosphere within the environmentally-controlled chamber 212 as the substrate 202 passes through the environmentally-controlled chamber 212. For example, the environmentally-controlled chamber 212 includes a humidifier, a de-humidifier, or any other suitable device for increasing or decreasing a humidity level within the environmentally-controlled chamber 212 as a portion of the substrate 202 that includes a mosquito egg (e.g., a damp portion of the substrate 202 on which a mosquito has laid an egg) passes through the environmentally-controlled chamber 212. As another example, the environmentally-controlled chamber 212 includes a drying device, a heating device, or any suitable device for providing an amount of heat within the environmentally-controlled chamber 212 to dry one or more mosquito eggs on a damp or wet portion of the substrate 202 as the portion of the substrate 202 passes through the environmentally-controlled chamber 212. In some examples, the devices within the environmentally-controlled chamber 212 can be used to adjust a parameter of the environment within the environmentally-controlled chamber 212 as mosquito eggs on the substrate 202 travel through the environmentally-controlled chamber 212, which can enhance one or more processes for mass rearing the mosquitos (e.g., by providing suitable environmental conditions for rearing the mosquito eggs or larva on a portion of the substrate 202 passing through the environmentally-controlled chamber 212).

At block 410, a driving force is applied to the roller of the plurality of rollers 204a-h to cause the substrate 202 to begin to travel along the path between the rollers 204a-h. In some examples, a drive unit 208 can apply the driving force to the roller to drive the rollers 204a-h and cause them to rotate, which causes the substrate 202 to travel along the path between the rollers 204a-h. As an example, a portion of the substrate 202 is wound around the roller 204h (e.g., at block 402) and the roller 204h is connected to the drive unit 208, which includes a motor, transmission, or other device for applying a rotational force to the roller 204h to drive the roller 204h and cause the roller 204h to rotate. Rotating the roller 204h causes the substrate 202 to rotate in a similar manner as the roller 204h, which causes the substrate 202 to unwind. The unwound or dispensed portion of the substrate 202 can then travel along a path from the roller 204a toward the roller 204h.

In some examples, the drive unit 208 can also control a rate or speed at which one or more of the rollers 204a-h rotates, which can affect a speed or velocity that the substrate 202 travels along a path between the rollers 204a-h. For example, the drive unit 208 can be communicatively coupled to a remote device (e.g., the computing device 300 of FIG. 3) and the remote device can transmit a signal to the drive unit 208. The signal can indicate a rotational speed of the drive unit 208, which can affect a speed or rate at which one or more of the rollers 204a-h will rotate. As an example, the signal can indicate a desired rotational speed of the drive unit 208, which affects the speed or rate that the roller 204h rotates. In some examples, the speed or rate at which the roller 204h rotates affects the speed or velocity with which the substrate 202 travels along the path between the rollers 204a-h. As an illustrative example, the signal transmitted from the remote device can cause the drive unit 208 to rotate at a rotational speed such that the roller 204h rotates and causes the substrate 202 to travel from the roller 204a toward the roller 204h at a rate of one-half inch per hour. As another illustrative example, the signal transmitted from the remote device can cause the drive unit 208 to apply no force to the roller 204h, which can cause the substrate 202 to stop moving and remain in a stationary position and, in some examples, the substrate 202 may remain in the stationary position until the remote device signals the drive unit 208 to apply a force to the roller 204h. Thus, in some examples, a motion of the substrate 202 or a speed at which the substrate 202 moves from the roller 204a to the roller 204h can be controlled by the drive unit 208 based on signals received by the drive unit 208.

While in the example above the substrate 202 is described as moving from the roller 204a toward the roller 204h at a rate of on-half inch per hour, the present disclosure is not limited to such configurations. Rather, the substrate 202 can travel between the rollers 204a-h at any speed or rate based on the application or use of the insect egg conveyor 200. For example, the rotational speed of the drive unit 208 may be based on a willingness of an insect (e.g., a mosquito) in the housing 218 to oviposit on a substrate 202 moving at a particular speed.

In some examples, the drive unit 208 can continuously apply a force to drive one or more of the rollers 204a-h to cause multiple (e.g., sequential) portions of the substrate 202 to contact fluid in the bath 206 as the substrate 202 travels from the roller 204a toward the roller 204h, which can provide various wet or damp locations on the substrate 202 on which the one or more mosquitos in the housing 218 can oviposit as the substrate 202 travels through the housing 218.

At block 412, data about an amount of mosquito eggs on a portion of the substrate 202 is detected by a sensor 214 of the insect egg conveyor 200. For example, the sensor 214 includes one or more cameras for capturing an image of a portion of the substrate 202 that includes one or more mosquito eggs. The sensor 214 can be communicatively coupled to a remote device (e.g., the computing device 300 of FIG. 3) and the sensor 214 can transmit data corresponding to the image to the remote device for determining an amount of mosquito eggs on the substrate 202 based on the image. As another example, the sensor 214 includes a scale or other suitable device for detecting a weight of a portion of the substrate 202 that includes one or more mosquito eggs. In such examples, the sensor 214 can be communicatively coupled to the remote device and transmit data that indicates the weight to the remote device for determining the amount of mosquito eggs on the portion of the substrate 202. For example, the remote device may include data about a weight of a portion of the substrate 202 prior to the portion of the substrate 202 traveling through the housing 218 (e.g., if a user programs the computing device 300 to include the data). The sensor 214 can detect a weight of the portion of the substrate 202 after the portion travels through the housing 218 and transmit data to the remote device indicating a weight of the portion of the substrate 202 after the portion travels through the housing 218. The remote device can compare the weight of the portion of the substrate 202 before and after traveling through the housing 218 to determine a weight of one or more mosquito eggs on the portion of the substrate 202, which can be used to determine an amount of mosquito eggs on the portion of the substrate 202.

At block 414, one or more mosquito eggs are removed and collected from the substrate 202 using a collection unit 216 of the insect egg conveyor 200. For example, the collection unit 216 includes a removal device 220 for removing the mosquito egg from the substrate 202 and a container 222 (e.g., a bin) for collecting the mosquito egg as the removal device 220 removes the mosquito egg from the substrate 202. The removal device 220 can include a brush or a scraper positioned proximate to the path of the substrate 202 for sweeping one or more mosquito eggs from a surface of the substrate 202. As another example, the removal device 220 can include an air blowing device that displaces air near the substrate 202 or blows air across the surface of the substrate 202 for removing one or more mosquito eggs from the surface of the substrate 202 (e.g., by blowing the air near the substrate 202 to displace the mosquito eggs from the surface of the substrate 202). In some examples, the air blowing device may blow deionized air toward the substrate 202 for removing one or more mosquito eggs from the surface of the substrate 202. The container 222 can be positioned proximate to the path of the substrate 202 and proximate to the removal device 220 for collecting at least a subset of the mosquito eggs removed from the surface of the substrate 202 by the removal device 220. In some examples, the container 222 can also include a scale for detecting a weight of the subset of the mosquito eggs for determining an amount of mosquito eggs in the subset. For example, the container 222 can detect a weight of the subset of the mosquito eggs and data indicating the weight can be transmitted to a remote device that can determine an amount of the mosquito eggs based on the weight.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect to any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. A system comprising:
   a roller positioned along a conveyor path;
   a hydrophilic substrate positioned on the roller;
   a fluid source positioned on the conveyor path to apply a fluid to the hydrophilic substrate; and
   a drive unit comprising a motor coupled to the roller to drive the roller and rotate the roller and move the hydrophilic substrate along the conveyor path and past the fluid source.

2. The system of claim 1, further comprising a remote computing device, wherein the drive unit is communicatively coupled to the remote device and the remote device comprises a processor and a memory, the memory comprising processor-executable program code configured to cause the processor to transmit a drive signal to the drive unit to control a speed of the hydrophilic substrate along the conveyor path.

3. The system of claim 2, wherein the memory comprises processor-executable program code configured to cause the processor to:
   transmit the drive signal to the drive unit to cause the drive unit to rotate at a first speed to move the hydrophilic substrate along the conveyor path.

4. The system of claim 1, wherein the hydrophilic substrate comprises at least one of paper, felt, or nylon cloth.

5. The system of claim 1, further comprising:
   a housing positioned on the conveyor path; and
   a population of insects located within the housing, and wherein rotating the roller causes the roller to move the hydrophilic substrate along the conveyor path and through the housing.

6. The system of claim 1, further comprising:
   a chamber positioned on the conveyor path, wherein rotating the roller causes the roller to move the hydrophilic substrate along the conveyor path and through the chamber and wherein the chamber comprises at least one of a humidifier or a de-humidifier to adjust a humidity level within the chamber.

7. The system of claim 1, further comprising:
   a chamber positioned on the conveyor path, wherein rotating the roller causes the roller to move the hydrophilic substrate along the conveyor path and through the chamber and wherein the chamber comprises at least one of a drying device or a heating device to provide an amount of heat to adjust a temperature within the chamber.

8. The system of claim 1, further comprising:
   a sensor positioned on the conveyor path; and
   a remote computing device in communication with the sensor, the remote computing device comprising a processor and a memory, the memory comprising processor-executable program code configured to cause the processor to:
   receive a sensor signal from the sensor; and
   determine an amount of mosquito eggs on a portion of the hydrophilic substrate based on the sensor signal.

9. The system of claim 8, wherein the sensor comprises a camera positioned on the conveyor path to capture an image of the hydrophilic substrate and mosquito eggs on the hydrophilic substrate and the sensor signal comprises the image.

10. The system of claim 8, wherein the sensor comprises a scale positioned on the conveyor path to detect a weight of the hydrophilic substrate and the amount of mosquito eggs on the hydrophilic substrate and the sensor signal comprises data about the weight, and wherein the processor determines the amount of mosquito eggs on the hydrophilic substrate based at least in part on the weight.

11. The system of claim 1, further comprising a collection unit positioned on the conveyor path, wherein the collection unit comprises at least one of a brush, a scraper, or a blower positioned on the conveyor path to remove an amount of mosquito eggs from a surface of the hydrophilic substrate.

12. The system of claim 11, wherein the collection unit further comprises a container positioned on the conveyor path and proximate to the brush, the scraper, or the blower to collect at least a portion of the amount of mosquito eggs removed from the surface of the hydrophilic substrate.

13. The system of claim 1, further comprising:
a fluid reservoir positioned proximate to the fluid source;
a sensor coupled to the fluid source to detect an amount of a fluid in the fluid source, wherein the sensor is communicatively coupled to a remote computing device to transmit a signal indicating the amount of the fluid in the fluid source and wherein the remote computing device comprises a processor to compare the amount of the fluid and a threshold amount of fluid and transmit a control signal to the fluid reservoir to cause the fluid reservoir to dispense fluid into the fluid source.

14. A method comprising:
positioning a hydrophilic substrate on a roller of an insect egg conveyor, the roller to move the hydrophilic substrate along a conveyor path;
positioning a fluid source on the conveyor path;
positioning an insect chamber on the conveyor path;
rotating the roller to move the hydrophilic substrate along the conveyor path, toward the fluid source, and through the insect chamber, wherein rotating the roller comprises driving, by a drive unit comprising a motor coupled to the roller, the roller to cause the roller to rotate; and
collecting eggs laid on the hydrophilic substrate by an insect in the insect chamber.

15. The method of claim 14, wherein the hydrophilic substrate comprises at least one of paper, felt, or nylon cloth.

16. The method of claim 14, wherein rotating the roller to move the hydrophilic substrate along the conveyor path further comprises transmitting, to the drive unit, a drive signal, the drive signal configured to cause the drive unit to rotate at a first speed to move the hydrophilic substrate along the conveyor path.

17. The method of claim 14, further comprising:
positioning a chamber of the insect egg conveyor on the conveyor path to allow the hydrophilic substrate to pass through the chamber; and
adjusting a humidity level within the chamber.

18. The method of claim 14, further comprising:
positioning a chamber of the insect egg conveyor on the conveyor path to allow the hydrophilic substrate to pass through the chamber; and
adjusting a temperature within the chamber.

19. The method of claim 14, further comprising transmitting, by a sensor positioned on the conveyor path, a sensor signal to a remote computing device.

20. The method of claim 19, wherein the sensor comprises a camera, and wherein providing the sensor signal comprises:
capturing, by the camera, an image of the hydrophilic substrate and the eggs laid on the hydrophilic substrate; and
transmitting the image to the remote computing device.

21. The method of claim 19, wherein the sensor comprises a scale positioned on the conveyor path and wherein providing the sensor signal comprises:
detecting, by the scale, a weight of the hydrophilic substrate and the eggs laid on the hydrophilic substrate; and
transmitting the weight to the remote computing device.

22. The method of claim 14, wherein collecting eggs laid on the hydrophilic substrate comprises:
removing, by a collection unit positioned on the conveyor path, eggs from the hydrophilic substrate; and
collecting, by the collection unit, eggs removed from the hydrophilic substrate, wherein the collection unit comprises:
at least one of a brush, a scraper, or a blower positioned on the conveyor path to remove an amount of eggs from the hydrophilic substrate; and
a container positioned on the conveyor path and proximate to the brush, the scraper, or the blower to collect at least a portion of the amount of eggs removed from the hydrophilic substrate.

23. The method of claim 22, wherein the container further comprises a sensor, the sensor comprising a scale and wherein the method further comprises:
detecting, by the sensor, a weight of the portion of the amount of eggs removed from the hydrophilic substrate; and
transmitting, by the sensor, the weight to a remote computing device.

24. The method of claim 14, further comprising:
positioning a fluid reservoir proximate to the fluid source; and
transmitting, by a sensor coupled to the fluid source, a signal indicating an amount of fluid in the fluid source to a remote computing device; and
receiving a control signal from the remote computing device to cause the fluid reservoir to dispense fluid into the fluid source.

* * * * *